(12) United States Patent
Takeuchi

(10) Patent No.: US 9,199,023 B2
(45) Date of Patent: Dec. 1, 2015

(54) OXYGENATOR

(71) Applicant: TERUMO KABUSHIKI KAISHA, Shibuya-ku (JP)

(72) Inventor: Kazuhiko Takeuchi, Fujinomiya (JP)

(*) Notice: Subject to any disclaimer, the term of this patent is extended or adjusted under 35 U.S.C. 154(b) by 0 days.

(21) Appl. No.: 14/041,434

(22) Filed: Sep. 30, 2013

(65) Prior Publication Data

US 2014/0030146 A1   Jan. 30, 2014

Related U.S. Application Data

(63) Continuation of application No. PCT/JP2012/057868, filed on Mar. 27, 2012.

(30) Foreign Application Priority Data

Mar. 31, 2011   (JP) ................. 2011-079884

(51) Int. Cl.
*A61M 1/16* (2006.01)
*B01D 63/02* (2006.01)
*B01D 71/26* (2006.01)
*B01D 69/08* (2006.01)

(52) U.S. Cl.
CPC ............. *A61M 1/1698* (2013.01); *B01D 63/02* (2013.01); *B01D 63/026* (2013.01); *B01D 69/081* (2013.01); *B01D 71/26* (2013.01)

(58) Field of Classification Search
CPC ... A61M 1/1698; B01D 63/02; B01D 63/026; B01D 69/081; B01D 71/26
USPC ..................... 422/44–48; 604/6.14
See application file for complete search history.

(56) References Cited

U.S. PATENT DOCUMENTS 5,552,047 A   9/1996   Oshida et al.
5,846,427 A   12/1998  Kessler et al.
(Continued)

FOREIGN PATENT DOCUMENTS

EP   0 895 786 A   2/1999
JP   11-047268 A   2/1999
(Continued)

OTHER PUBLICATIONS

International Search Report (PCT/ISA/210) mailed on May 15, 2012, by the Japanese Patent Office as the International Searching Authority for International Application No. PCT/JP2012/057868.
(Continued)

*Primary Examiner* — Philip R Wiest
*Assistant Examiner* — Benjamin Klein
(74) *Attorney, Agent, or Firm* — Buchanan Ingersoll & Rooney PC

(57) ABSTRACT

An oxygenator includes a housing; a hollow fiber membrane layer that is stored in the housing and has multiple integrated hollow fiber membranes with a gas exchange function; a gas inlet portion and a gas outlet portion that are provided on the upstream and downstream of gas passages in lumens of the hollow fiber membranes, respectively; and a blood inlet portion and a blood outlet portion that are provided on the upstream and downstream of blood passages outsides of the hollow fiber membranes, respectively. The hollow fiber membranes in the hollow fiber membrane layer are fixed relative to each other at one end portion and the other end portion thereof. Conditions $30 \leq \epsilon \leq 60$ and $OD \leq 4.5 \times \epsilon$ are met where $\epsilon$ [μm] is an average separation distance between the adjacent hollow fiber membranes at a fixed portion of the hollow fiber membrane layer and OD [μm] is the outer diameter of the hollow fiber membrane.

14 Claims, 11 Drawing Sheets

(56) References Cited

U.S. PATENT DOCUMENTS

| | | | |
|---|---|---|---|
| 6,387,324 B1 * | 5/2002 | Patterson et al. | 422/45 |
| 2009/0175762 A1 * | 7/2009 | Ogihara et al. | 422/45 |
| 2010/0135852 A1 * | 6/2010 | Kawakatsu et al. | 422/48 |

FOREIGN PATENT DOCUMENTS

| | | |
|---|---|---|
| JP | 11-299884 A | 11/1999 |
| JP | 3396085 B2 | 4/2003 |
| JP | 3936376 B2 | 6/2007 |
| JP | 4026037 B2 | 12/2007 |
| JP | 4366268 B2 | 11/2009 |

OTHER PUBLICATIONS

The Extended Search Report issued by the European Patent Office on Jan. 26, 2015 in corresponding European Application No. 12765191.7 (5 pages).

* cited by examiner

OXYGENATOR

CROSS REFERENCE TO RELATED APPLICATIONS

This application claims priority as a continuation application under 35 U.S.C. §120 to International Application No. PCT/JP2012/057868 filed on Mar. 27, 2012, designating the U.S., and which claims priority to Japanese Application No. 2011-079884 filed on Mar. 31, 2011, the entire content of which is incorporated herein by reference.

TECHNICAL FIELD

The present invention relates to oxygenators.

BACKGROUND ART

Conventionally, there has been known oxygenators configured to conduct gas exchange using a hollow fiber membrane layer with multiple integrated hollow fiber membranes, as shown, for example, in JP4366268. The oxygenator disclosed in JP4366268 has a housing, an entirely circular cylindrical hollow fiber membrane layer stored in the housing, a blood inlet, a blood outlet, a gas inlet, and a gas outlet, wherein gas exchange, that is, oxygenation and decarbonation, takes place between blood and gas via the hollow fiber membranes.

There is a demand for oxygenators in which the filling amount of blood is decreased to reduce the amount of blood circulating extracorporeally.

In conventional oxygenators, however, the filling amount of blood cannot be reduced without lowering gas exchange performance and increasing a pressure loss during flowing of the blood.

It would be advantageous to provide an oxygenator with favorable gas exchange performance that creates a relatively small pressure loss during flowing of blood and needs only a small filling amount of blood.

SUMMARY

The disclosure herein relates to an oxygenator, including: a housing, a hollow fiber membrane layer that is stored in the housing and has multiple integrated hollow fiber membranes with a gas exchange function, a gas inlet portion and a gas outlet portion that are provided on the upstream and downstream of gas passages in lumens of the hollow fiber membranes, respectively, and a blood inlet portion and a blood outlet portion that are provided on the upstream and downstream of blood passages outsides of the hollow fiber membranes, respectively, wherein the hollow fiber membranes in the hollow fiber membrane layer are fixed to each other at one end and the other end thereof, and conditions $30 \leq \epsilon \leq 60$ and $OD \leq 4.5 \times \epsilon$ are met where $\epsilon$ [μm] is an average separation distance between the adjacent hollow fiber membranes at a fixed portion of the hollow fiber membrane layer and OD [μm] is the outer diameter of the hollow fiber membranes.

In an exemplary embodiment of the oxygenator of the disclosure here, condition $0.55 \times OD \leq ID \leq 0.8 \times OD$ is preferably met where ID [μm] is the inner diameter of the hollow fiber membranes.

In an exemplary embodiment of the oxygenator of the disclosure here, condition $L \leq 1.3 \times ID$ is preferably met where ID [μm] is the inner diameter of the hollow fiber membranes and L [mm] is the length of the hollow fiber membranes contributing to gas exchange.

Further, in an exemplary embodiment of the oxygenator of the disclosure here, the amount of blood filled in the housing is preferably 25 to 50 mL/m² per unit membrane area.

The hollow fiber membranes are preferably formed by porous polypropylene or polymethylpentene in an exemplary embodiment of the disclosure, and it is preferred that the entire shape of the hollow fiber membrane layer is substantially cuboidal.

It is also preferred that the entire shape of the hollow fiber membrane layer is substantially cylindrical in a further exemplary embodiment of the disclosure.

BRIEF DESCRIPTION OF DRAWINGS

The accompanying drawings are included in the specification and form a part of the disclosure herein, and are used to disclose aspects and principles of the disclosure here together with the detailed description set forth below.

DETAILED DESCRIPTION

Preferred exemplary embodiments of an oxygenator of the disclosure herein will be described below in detail with reference to the attached drawings.

Figure 1:
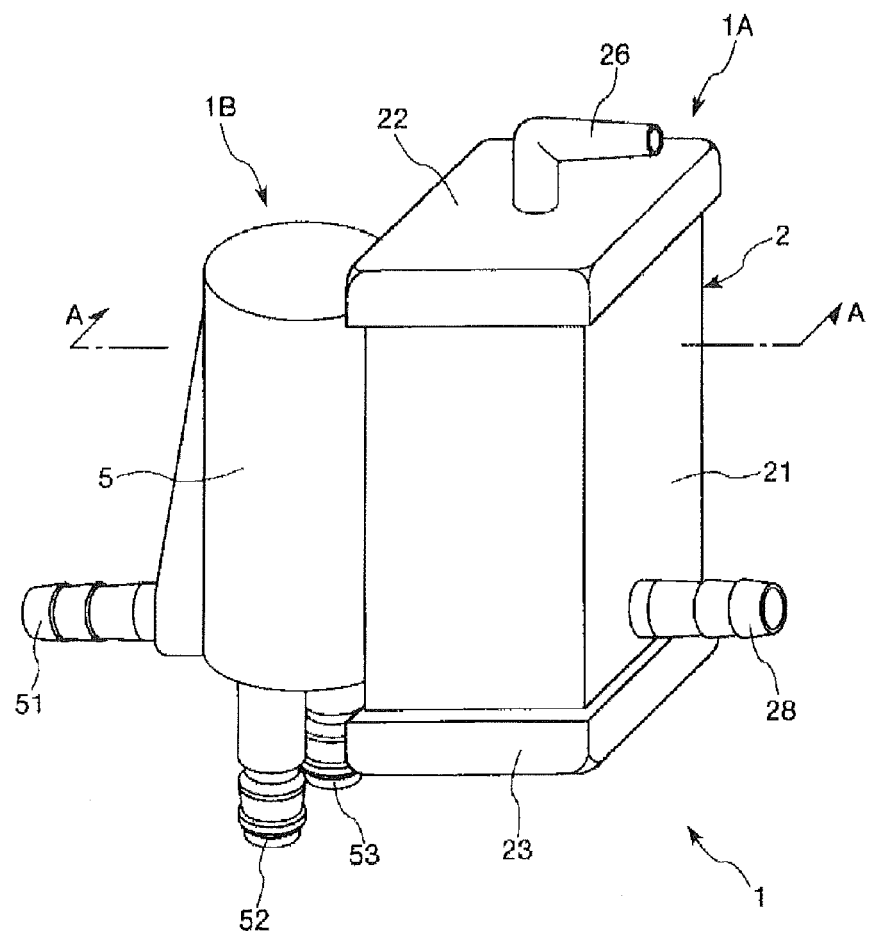
FIG. 1 is a perspective view of a first exemplary embodiment of an oxygenator of the disclosure here.
Figure 2:
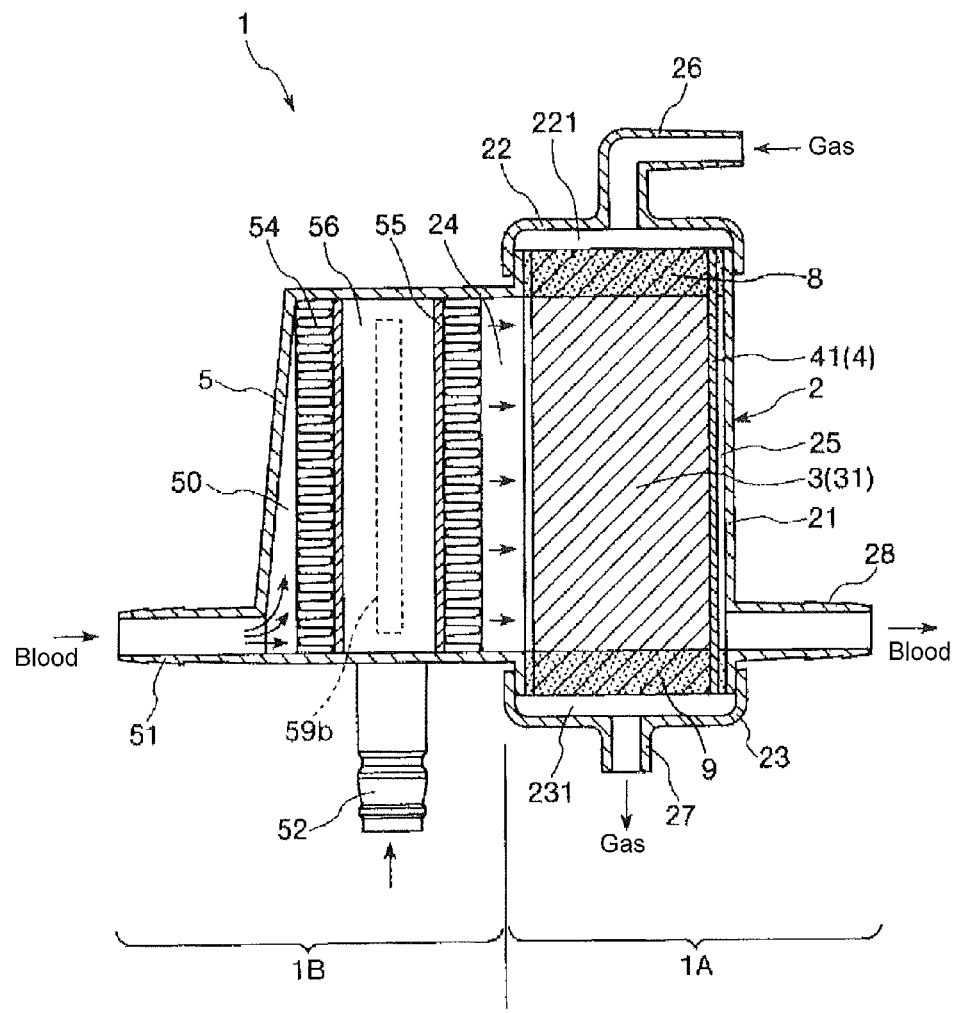
FIG. 2 is a cross section view of FIG. 1 taken along line A-A.
Figure 5:
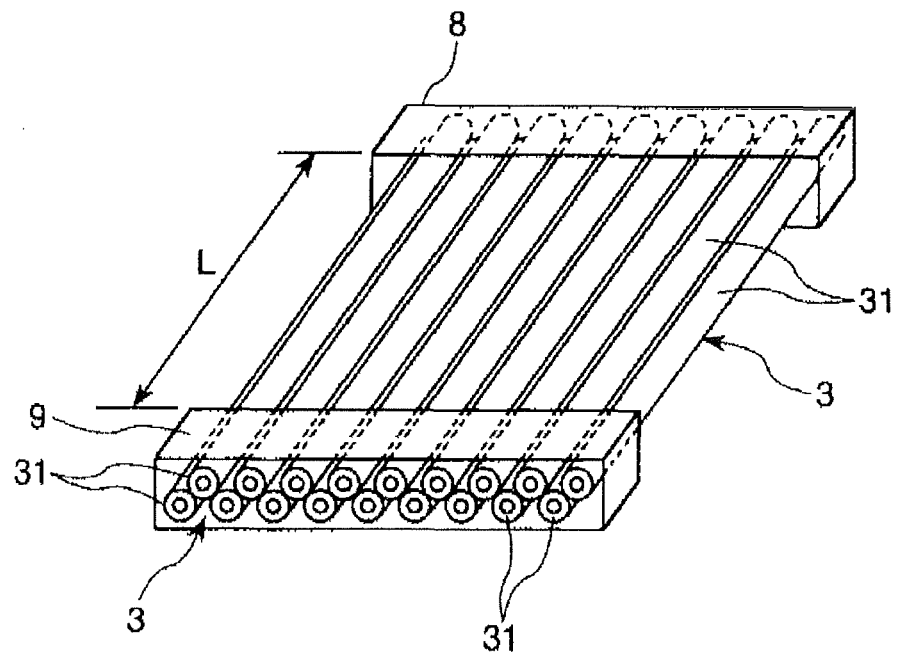
FIG. 5 is a schematic perspective view of a hollow fiber membrane layer and partition walls in the oxygenator illustrated in FIG. 1.

In FIGS. 1 and 2, the upper side is referred to as "upper" or "above," the lower side is referred to as "lower" or "below," the left side is referred to as "blood inlet side" or "upstream," and the right side is referred to as "blood outlet side" or "downstream." The number of hollow fiber membranes shown in FIG. 5 is for illustrative purposes and the actual number may differ therefrom.

The oxygenator 1 in the exemplary embodiment illustrated in FIGS. 1 to 6 is a heat exchanger-equipped oxygenator that includes an oxygenating portion 1A adapted to perform gas exchange with blood and a heat exchange portion (heat exchanger) 1B adapted to perform heat exchange with blood. This oxygenator can be set up in a blood extracorporeal circuit, for example.

The oxygenator 1 includes a housing 2 located on the oxygenating portion 1A side, and a heat exchanger housing 5 located on the heat exchange portion 1B side. These housings are connected (joined) or integrated with each other.

The housing 2 of the oxygenating portion 1A includes a housing body formed in a square cylinder, that is, having a square (quadrate or rectangular) cross section (hereinafter, referred to as "square cylindrical housing body") 21, a dish-shaped first header (upper lid) 22 that closes an upper end opening of the square cylindrical housing body 21, and a dish-shaped second header (lower lid) 23 that closes a lower end opening of the square cylindrical housing body 21.

The square cylindrical housing body 21, the first header 22, and the second header 23 are each formed from a polyolefin such as polyethylene or polypropylene, ester resin (for example, polyester such as polyethylene terephthalate or polybutylene terephthalate), styrene resin (for example, polystyrene, MS resin, MBS resin, ABS resin or BS resin), resin materials such as polycarbonate, various kinds of ceramic materials, metal materials, or the like. The first header 22 and the second header 23 are preferably secured to the square cylindrical housing body 21 by adhesion means such as fusing, adhesion using an adhesive, or the like.

The square cylindrical housing body 21 has a circular tube-shaped blood outlet port (blood outlet port) 28 projecting from the lower portion thereof on the blood outlet side. The first header 22 has a tubular gas inlet port 26 projecting from the upper portion thereof. The second header 23 has a tubular gas outlet port 27 projecting from the lower portion thereof. The gas inlet port 26 is preferably bent at substantially a right angle such that the tip end portion thereof is parallel with the blood outlet port 28.

As described above, one skilled in the art will appreciate that the entire shape of the housing 2 is substantially cuboid. Due to the shape of the housing 2, the oxygenator 1 of the disclosure here provides at least the following advantages. Specifically, the housing 2 is cuboid-shaped and can thus efficiently store hollow fiber membranes 31 therein with less dead space to allow efficient gas exchange in the small-sized oxygenator 1. The housing 2 also has a flat outer surface, and thus the housing 2 can be fixed to a fixation substrate in a ready and reliable manner. Further, the interior of the housing 2 is defined by flat surfaces, and thus the hollow fiber membranes 31 can be stored in the housing 2 while preventing application of a load on the hollow fiber membranes 31 from bending the hollow fiber membranes 31 or the like.

In the exemplary embodiment of the disclosure herein, the entire shape of the housing 2 is not necessarily a complete cuboid, but may have chamfered or rounded portions at all or some of corners thereof. Alternatively, the housing 2 may be partially cut away or provided with a different-shaped portion.

Figure 3:
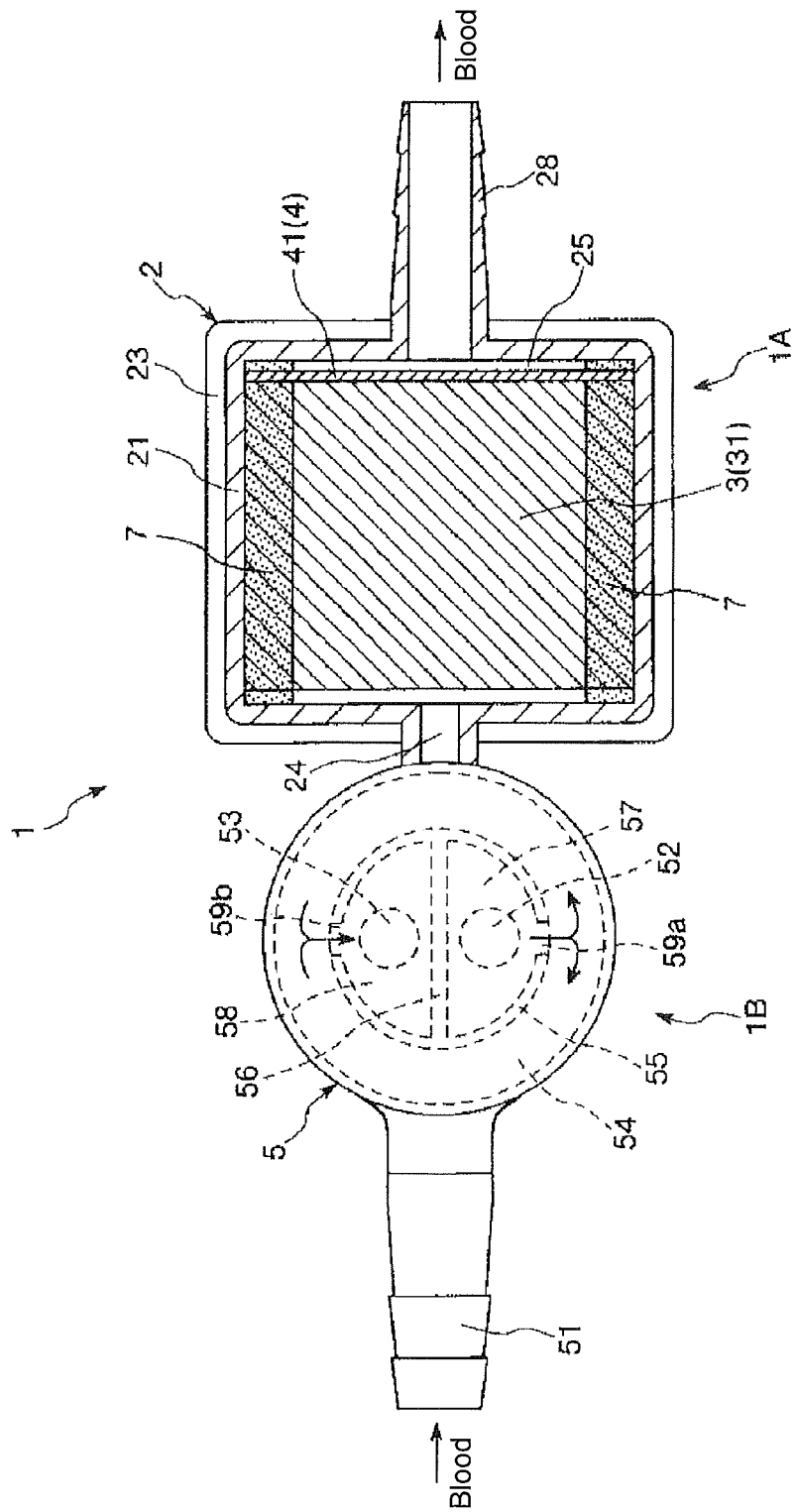
FIG. 3 is a transverse cross section view of an oxygenating portion in the oxygenator illustrated in FIG. 1.
Figure 4:
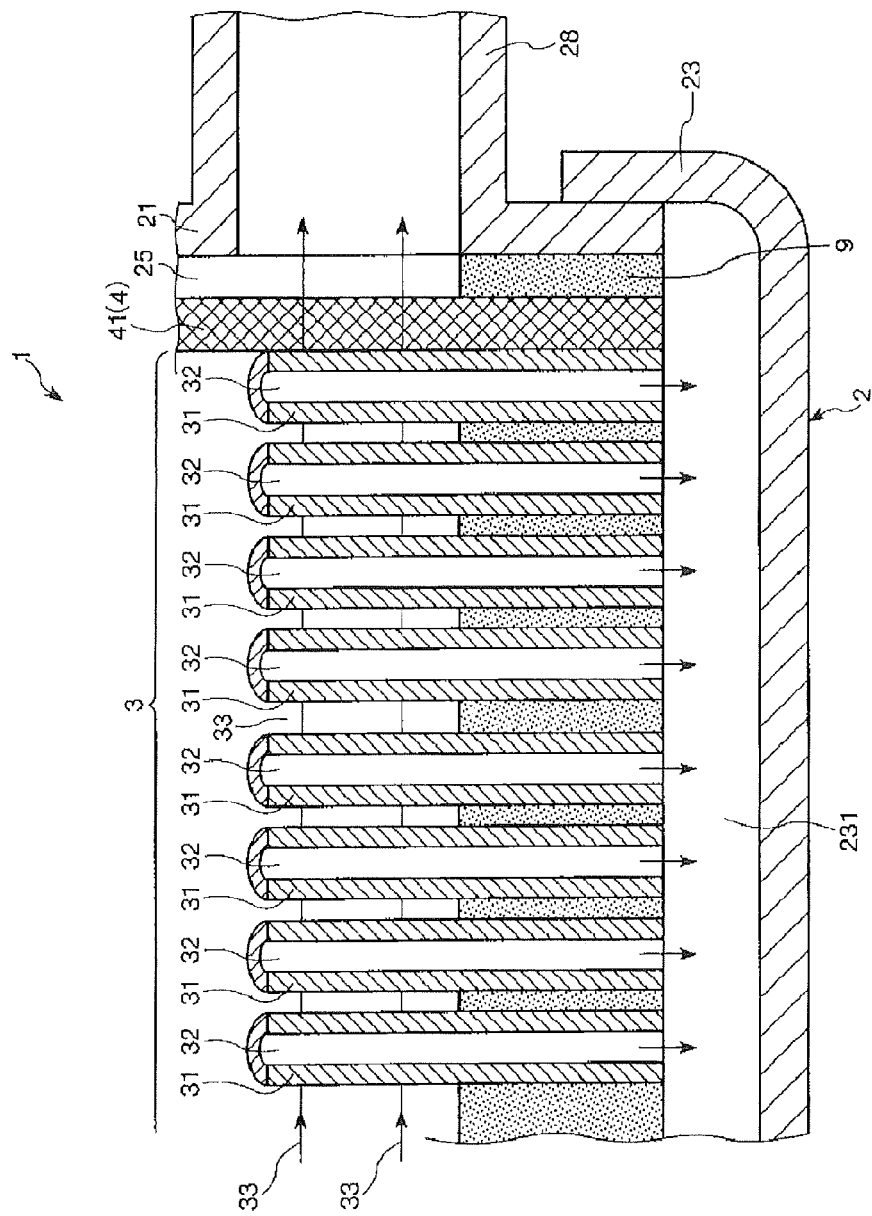
FIG. 4 is an enlarged cross section view of a right lower portion of FIG. 2 (a hollow fiber membrane layer and a filter member).

As illustrated in FIGS. 2 to 4, the housing 2 has therein a hollow fiber membrane layer 3 including multiple integrated hollow fiber membranes 31 with a gas exchange function, and a filter member 41 serving as a bubble removal means 4 provided on the blood outlet port 28 (blood outlet portion) side of the hollow fiber membrane layer 3. The hollow fiber membrane layer 3 and the filter member 41 are arranged from the blood inlet side in order of the hollow fiber membrane layer 3 and the filter member 41.

As illustrated in FIG. 4, most of the hollow fiber membranes 31 constituting the hollow fiber membrane layer 3 are substantially parallel to one another. In this case, the hollow fiber membranes 31 are each placed with the longer sides thereof along the up-down direction (vertical direction).

The arrangement pattern, arrangement direction, etc., of the hollow fiber membranes 31 in the hollow fiber membrane layer 3 are not limited to the aforementioned embodiments. For example, the hollow fiber membranes 31 may be arranged in the horizontal direction, the hollow fiber membranes 31 may have portions at which the hollow fiber membranes 31 obliquely intersect one another (crossing portions), all or some of the hollow fiber membranes 31 may be curved, or all or some of the hollow fiber membranes 31 may be arranged in a corrugated, helical, spiral, or annular form.

Both ends of the hollow fiber membranes 31, i.e., an upper end portion (one end portion) and a lower end portion (the other end portion) are fixed to inner surfaces of the square rectangular housing body 21 by way of partition walls 8 and 9 (see FIG. 2). Accordingly, both end portions of each hollow fiber membranes 31 are fixed relative to each other, respectively. The partition walls 8 and 9 are formed by a potting material, for example, polyurethane or silicone rubber, or an adhesive.

Both ends of the hollow fiber membrane layer 3 are fixed (secured) by securing portions 7 to inner surfaces of the square rectangular housing body 21 (see FIG. 3). The securing portions 7 are formed from the same material (potting material or another adhesive) as that used for the partition walls 8 and 9.

A first chamber 221 is defined by the first header 22 and the partition wall 8. The first chamber 221 is a gas inlet chamber into which gas flows. The hollow fiber membranes 31 have upper end openings opened to and communicating with the first chamber 221.

A second chamber 231 is defined by the second header 23 and the partition wall 9. The second chamber 231 is a gas outlet chamber from which gas flows out. The hollow fiber membranes 31 have lower end openings opened to and communicating with the second chamber 231 (see FIG. 4).

Lumens of the hollow fiber membranes 31 form gas passages 32 through which gas flows. The gas inlet port 26 and the first chamber 221 constitute a gas inlet portion located on the upstream of the gas passages 32. The gas outlet port 27 and the second chamber 231 constitute a gas outlet portion located on the downstream of the gas passages 32.

The hollow fiber membrane layer 3 fills the square cylindrical housing body 21 substantially without any extra space, and thus the hollow fiber membrane layer 3 is almost entirely shaped as a cuboid. This provides high efficiency of filling the hollow fiber membranes 31 into the similarly shaped square cylindrical housing body 21 (with less dead space), which contributes to a smaller size and higher performance of the oxygenating portion 1A.

The hollow fiber membranes 31 are exposed between the partition walls 8 and 9 in the housing 2 to form blood passages 33 outside the hollow fiber membranes 31, that is, in the gaps between the hollow fiber membranes 31 to allow blood to flow from the left to right sides in FIGS. 2 to 4.

On the upstream side of the blood passages 33 (upstream of the hollow fiber membrane layer 3), that is, at a connection portion between the square cylindrical housing body 21 and the heat-exchanger housing 5, a band-shaped or slit-shaped blood inlet-side opening (blood inlet-side space) 24 is formed as a blood inlet portion extending in the vertical direction (substantially parallel to the direction of placement of the hollow fiber membranes 31). The interior of the housing 2 and the interior of the heat exchanger housing 5 communicate with each other via the blood inlet-side opening 24. The foregoing configuration allows efficient transfer of blood from the heat exchanger 1B to the oxygenating portion 1A.

The length of the blood inlet-side opening 24 (vertical length) is preferably substantially equal to (see FIG. 2) or slightly smaller than an effective length of the hollow fiber membranes 31 (from the lower surface of the partition wall 8 to the upper surface of the partition wall 9) (70% or more of the effective length). This allows efficient transfer of blood from the heat exchanger 1B to the oxygenating portion 1A and efficient gas exchange with blood in the blood passages 33.

At least in a part of the upstream side (blood inlet-side opening 24 side) of the blood passages 33, the direction of flow of blood is substantially orthogonal to the longitudinal sides of the hollow fiber membranes 31. This allows efficient gas exchange with blood flowing through the blood passages 33.

Downstream of the blood passages 33 (on the downstream-side surface of the hollow fiber membrane layer 3), a gap is formed between the filter member 41 and the inner surface of the square cylindrical housing body 21. The gap functions as a blood outlet-side opening (blood outlet-side space) 25. The blood outlet-side opening 25 and the blood outlet port 28 communicating with the blood outlet-side opening 25 constitute a blood outlet portion. The blood outlet portion with the blood outlet-side opening 25 provides a space for the blood having flowed through the filter member 41 to flow toward the blood outlet port 28, thereby allowing smooth discharge of blood.

The hollow fiber membrane layer 3, the filter member 41, and the blood passages 33 are disposed between the blood inlet-side opening 24 and the blood outlet-side opening 25.

The hollow fiber membranes 31 use porous gas exchange films, for example. The porous hollow fiber membranes may have a wall thickness of about 5 to 200 μm, preferably 10 to 100 μm, a porosity of about 20 to 80%, preferably about 30 to 60%, a pore size of about 0.001 to 5 μm, preferably about 0.002 to 1 μm.

A constituent material for the hollow fiber membranes 31 is a hydrophobic polymer material, for example, polypropylene, polyethylene, polysulfone, polyacrylonitrile, polyterafluoroethylene, or polymethyl pentane. Polyolefin resin is preferred, and polypropylene or polymethylpentene is more preferred. The constituent material is more preferably configured such that pores are formed in the wall of the material by stretching or solid-liquid phase separation. Specifically, porous polypropylene or polymethylpentene are preferred.

Figure 6:
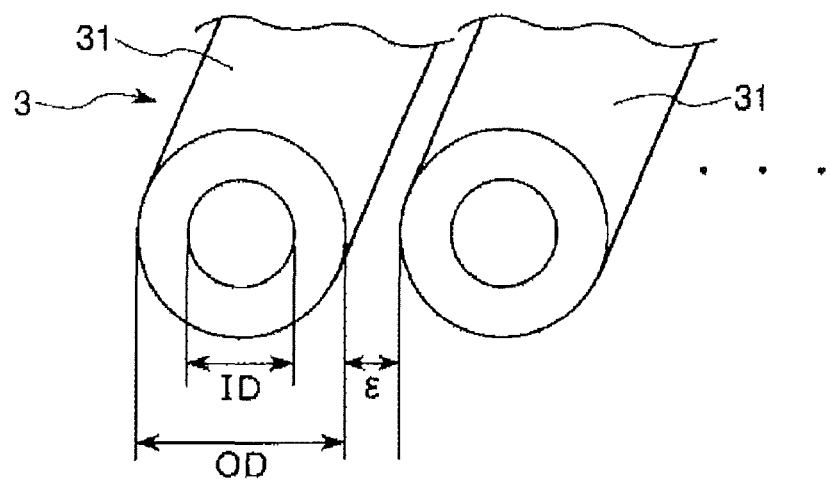
FIG. 6 is a perspective view of hollow fiber membranes in the oxygenator illustrated in FIG. 1.

In addition, as illustrated in FIGS. 5 and 6, the hollow fiber membrane layer 3 is configured to meet the conditions described below where $\epsilon$ [μm] is an average separation distance between the adjacent hollow fiber membranes 31 at opposite end portions of the hollow fiber membrane layer 3, that is, the portions of the hollow fiber membrane layer 3 fixed by the partition walls 8 and 9, OD [μm] is the outer diameter of the hollow fiber membranes 31, ID [μm] is the inner diameter of the hollow fiber membranes 31, and L [mm] is the length of the portions of the hollow fiber membranes 31 not fixed by the partition walls 8 and 9, that is, the length of the portions of the hollow fiber membranes 31 contributing to gas exchange (effective length). In the following description, the length of the portions of the hollow fiber membranes 31 contributing to gas exchange will also be referred to as simply "effective length." The length of the hollow fiber membranes 31 is measured along the bodies of the hollow fiber membranes 31, and for example, when the hollow fiber membranes 31 are wound in a spiral manner, the length of the hollow fiber membranes 31 is measured along the spiral. The average separation distance c is along one direction, the horizontal direction in the configurations illustrated in FIGS. 5 and 6. That is, the hollow fiber membranes 31 aligned in the vertical direction illustrated in FIG. 5 are in contact with each other, and data on the hollow fiber membranes 31 are not used in calculation of the average separation distance $\epsilon$.

First, the average separation distance $\epsilon$ [μm] and the outer diameter OD [μm] of the hollow fiber membranes 31 are set to meet the following conditions:

$$30 \le \epsilon \le 60 \text{ and } OD \le 4.5 \times \epsilon$$

When the average separation distance $\epsilon$ and the outer diameter OD are set within the foregoing ranges, it is possible to decrease the amount of blood filled in the oxygenating portion 1A and thus reduce the amount of blood filled in the oxygenator 1, without lowering gas exchange performance or increasing a pressure loss during flowing of the blood.

That is, when the average separation distance $\epsilon$ is larger than the foregoing upper limit value, the gas exchange performance is lowered. When the average separation distance $\epsilon$ is smaller than the lower limit value, the pressure loss increases during flowing of the blood.

When the outer diameter OD of the hollow fiber membranes 31 is larger than the foregoing upper limit value, the filling amount of blood is increased.

The separation distance between the hollow fiber membranes 31 at portions of the hollow fiber membranes 31 contributing to gas exchange corresponds to the separation distance between the hollow fiber membranes 31 at the opposite end portions of the hollow fiber membranes 31. Accordingly, the average separation distance $\epsilon$ is defined by the opposite end portions of the hollow fiber membranes 31.

In the hollow fiber membrane layer 3, it is preferred that the average separation distance between the hollow fiber membranes 31 at the upper end portions thereof and the average separation distance between the hollow fiber membranes 31 at the lower end portions thereof are equal to each other. This allows efficient flowing of blood.

In an exemplary embodiment of the disclosure, the average separation distance $\epsilon$ [μm] is preferably $30 \le \epsilon \le 60$, more preferably $35 \le \epsilon \le 55$, and the outer diameter OD [μm] of the hollow fiber membranes 31 is preferably $100 \le OD \le 4.5 \times \epsilon$, more preferably $100 \le OD \le 270$, further preferably $120 \le OD \le 220$.

Although it is not particularly limited, the inner diameter ID [μm] of the hollow fiber membranes 31 is preferably $0.55 \times OD \le ID \le 0.8 \times OD$, more preferably $60 \le ID \le 160$.

Accordingly, it is possible to make the pressure loss relatively small during flowing of gas into the lumens of the hollow fiber membranes 31 while maintaining the strength of the hollow fiber membranes 31. Specifically, when the inner diameter ID of the hollow fiber membranes 31 is larger than the foregoing upper limit value, the hollow fiber membranes 31 are thinner and may be lowered in strength depending on other conditions. When the inner diameter ID is smaller than the foregoing lower limit value, a pressure loss may be larger during flowing of gas into the lumens of the hollow fiber membranes 31 depending on other conditions.

Although it is not particularly limited, in an exemplary embodiment of the disclosure, the effective length L [mm] of the hollow fiber membranes 31 is preferably $L \le 1.3 \times ID$, more preferably $50 \le L \le 1.3 \times ID$, further preferably $50 \le L \le 200$.

Accordingly, it is possible to make the pressure loss relatively small during flowing of gas into the lumens of the hollow fiber membranes 31. Specifically, when the effective length L of the hollow fiber membranes 31 is larger than the foregoing upper limit value, a pressure loss during flowing of gas into the lumens of the hollow fiber membranes 31 may be large depending on other conditions.

Although the disclosure is not particularly limited thereto, the thickness of the hollow fiber membrane layer 3 (horizontal length in FIG. 2) is preferably about 10 to 100 mm, more preferably about 20 to 80 mm.

Although the disclosure is not particularly limited thereto, the width of the hollow fiber membrane layer 3 (vertical length in FIG. 3) is preferably about 10 to 100 mm, more preferably about 20 to 80 mm.

Although the disclosure here is not particularly limited on a method for manufacturing the hollow fiber membranes 31, the hollow fiber membranes 31 with predetermined outer and inner diameters can be manufactured using a drawing method or a solid-liquid phase separation method, for example, to adjust as appropriate conditions such as spinning speed, the amount of resin ejected, and the like.

In addition, the disclosure here is not particularly limited on a method for forming the hollow fiber membrane layer 3 by aligning the hollow fiber membranes 31 with a predetermined separation distance therebetween. As an example, when the hollow fiber membranes 31 are to be arranged in a helical form, a system is used including a rotation device rotating a tubular core around which the hollow fiber membranes 31 are to be wound, and a winder device. At least one of the rotation device and the winder device moves in the axial direction of the core. In addition, the separation distance between the adjacent hollow fiber membranes 31 in the system is set at an average separation distance $\epsilon$. Then, while the rotation device and/or the winder device is moved in the axial direction of the core, the winder device feeds the hollow fiber membranes 31 and the rotating device rotates the core. Accordingly, the hollow fiber membranes 31 are wound in a helical form around the core with the average separation distance $\epsilon$. The hollow fiber membranes 31 may be wound one by one or in multiples at the same time.

When the hollow fiber membranes 31 are arranged in a helical form, the central axes of the hollow fiber membranes 31 may be oriented in the vertical direction or inclined with respect to the vertical direction at upper and lower end portions thereof.

In the oxygenator 1, providing the hollow fiber membrane layer 3 makes it possible to set the amount of blood filled in the housing 2, that is, the amount of blood filled in the oxygenating portion 1A per unit membrane area of the oxygenator 1 at, for example, about 25 to 50 mL/m², in particular, about 30 to 45 mL/m².

Therefore, the amount of blood filled in the oxygenator 1 may be about 30 to 90 mL/m², in particular, 35 to 85 mL/m², for example, depending on the amount of blood filled in the heat exchange portion 1B and the like.

As described above, the bubble removal means 4 having the function of catching bubbles in the blood and removing the same from the blood is provided downstream (blood outlet portion side) of the hollow fiber membrane layer 3. As illustrated in FIGS. 2 to 4, the bubble removal means 4 has a filter member 41.

The filter member 41 has the function of catching bubbles existing in blood flowing through the blood passages 33.

The filter member 41 is formed by a substantially rectangular, flat sheet-like member (hereinafter, also referred to simply as "sheet"), and is fixed to the housing 2 by being secured at the edges thereof (four sides) along the partition walls 8 and 9 and the respective securing portions 7.

In the illustrated embodiment, the plane shape of the filter member 41 is rectangular (or square). However, the plane shape of the filter member 41 is not limited to this but may be a trapezoid, parallelogram, oval, elongated circle, or the like.

In the illustrated embodiment, the filter member 41 is configured as a flat sheet. However, the filter member 41 is not limited to this configuration and may not necessarily be flat. For example, the filter member 41 may be entirely or partially curved, or deformed in a corrugated or bellows shape or the like.

The filter member 41 has a single surface thereof which is in contact with a surface downstream (blood outlet portion side) of the hollow fiber membrane layer 3 so as to substantially cover the entire surface. Providing the filter member 41 in this manner makes it possible to increase the effective area of the filter member 41 and allow the filter member 41 to exert a sufficient capability for catching bubbles. In addition, when the effective area of the filter member 41 is larger, even if the filter member 41 is partly clogged (with adhesion of clots of blood, for example), it is possible to prevent (suppress) interference with the entire flow of blood.

The gap, that is, the blood outlet-side opening 25, is formed between the filter member 41 and the housing 2 (see FIGS. 2 to 4). It is thus possible to suppress contact (close adhesion) of the filter member 41 with the inner surface of the housing 2. Accordingly, the blood having flowed through the filter member 41 can easily flow downward in the blood outlet-side opening 25 and smoothly flow toward the blood outlet port 28.

The oxygenator 1 having the thus arranged filter member 41 is used in an exemplary configuration illustrated in FIG. 2. In this case, the blood outlet port 28 is positioned at a vertically lower portion of the oxygenator 1 in use. Specifically, the lumen of the blood outlet port 28 communicates with the lower portion of the blood outlet-side opening 25. The blood having flowed through the filter member 41 and entered into the blood outlet-side opening 25 flows downward in the blood outlet-side opening 25 and flows out from the blood outlet port 28 to the outside of the housing 2.

Even when bubbles exist in the blood flowing through the blood passages, the filter member 41 can catch the bubbles. In addition, the bubbles caught by the filter member 41 are pressed by the blood and entered into the hollow fiber membranes 31 near the filter member 41, and as a result, the bubbles are removed from the blood passages 33.

The filter member 41 may be configured in a form of mesh (net), woven cloth, non-woven cloth, or any combination of the foregoing, for example. Among the foregoing forms, a mesh (net) form is preferred and a screen filter is in particular preferred. This makes it possible to catch bubbles in a reliable manner using the two filter members and thereby facilitate smooth flow of the blood.

When the filter member 41 is configured in a mesh form, though it is not particularly limited, the mesh size is preferably in general equal to or less than 80 µm, more preferably about 15 to 60 µm, in particular preferably 20 to 45 µm. This makes it possible to catch relatively fine bubbles without increasing the flow resistance of the blood and provide a high efficiency of catching bubbles (removal capability).

The constituent material of the filter member 41 may be, for example, polyolefin such as polyamide, polyethylene, or polypropylene, polyester such as polyethylene terephthalate or polybutylene terephthalate, nylon, cellulose, polyurethane, aramid fiber, or the like. In particular, polyethylene terephthalate, polyethylene, or polyurethane are preferably used as constituent material for the filter members because these materials are excellent in resistance to blood clotting and are less prone to cause clogging.

The filter member 41 is preferably hydrophilic. Specifically, the filter member 41 is preferably formed by a hydrophilic material or subjected to a hydrophilicity process (for example, plasma treatment, coating or the like). This facilitates removal of bubbles upon priming of the oxygenator 1. In addition, when the blood mixed with bubbles flows, the bubbles are further unlikely to flow, which more reliably prevents outflow of bubbles from the blood outlet port 28 so as to improve the bubble removal capability of the filter member 41.

The filter member 41 may be formed as a single sheet (in particular, a mesh such as a screen filter) or two or more stacked sheets. When two or more sheets are stacked, the sheets are preferably different in at least one condition such as form, constituent material, mesh size, flat/non-flat state, plane shape, and the like. This is because combining the different conditions is advantageous in providing the filter member 41 with a variety of (multiplicity) functions and further improving the bubble removal capability. For example, when the filter member 41 is formed by two stacked meshes which differ in mesh size (the mesh with the larger mesh size is located on the upstream side), it is possible to first catch relatively large bubbles at the mesh with the larger mesh size and then catch fine bubbles having flowed through that mesh with the mesh with a smaller mesh size. This improves the bubble removal capability without increasing the flow resistance of the blood.

Next, the heat exchange portion (heat exchanger) 1B will be described. The heat exchanger 1B has the heat exchanger housing 5. The heat exchanger housing 5 is substantially cylinder-shaped and closed at upper and lower ends thereof. The heat exchanger housing 5 has a blood chamber 50 therein. The heat exchanger housing 5 has a tubular heat medium inlet port 52 and a heat medium outlet port 53 protruding from a lower end (lower surface) thereof. In addition, the heat exchanger housing 5 has a tubular blood inlet port 51 protruding from a lower portion at the left side thereof as illustrated in FIG. 2. The lumen of the blood inlet port 51 communicates with the blood chamber 50.

The heat exchanger housing 5 has therein an entirely cylindrical heat exchange body 54, a circular cylindrical heat medium chamber forming member (circular cylindrical wall) 55 arranged on an inner periphery of the heat exchange body 54, and a separation wall 56 separating the inner space of the heat medium chamber forming member 55 into an inlet-side heat medium chamber 57 and an outlet-side heat medium chamber 58. The heat medium chamber forming member 55 has the function of forming a heat medium chamber inside of the heat exchange body 54 for temporarily reserving heat medium, and the function of restricting deformation of the cylindrical heat exchange body.

The heat medium chamber forming member 55 and the separation wall 56 are fixed to the heat exchanger housing 5 by fusing, adhering with an adhesive, or the like, for example. The heat medium chamber forming member 55 and the separation 56 may be separately or integrally formed.

The heat medium chamber forming member 55 has band-like openings 59a and 59b extending in the vertical direction and penetrating the wall portion of the heat medium chamber forming member 55. The openings 59a and 59b are opposed to each other with the separation wall 56 therebetween (see FIG. 3). The opening 59a communicates with the inlet-side heat medium chamber 57, and the opening 59b communicates with the outlet-side heat medium chamber 58.

The heat exchange body 54 may use a so-called bellows-type heat exchange body (bellows tube) as illustrated in FIG. 2. The bellows-type heat exchange body 54 includes a bellows forming portion with multiple hollow annular projections substantially parallel to the side surface of the axially central portion thereof, and a cylindrical portion formed at opposite ends (upper and lower ends) thereof and having an inner diameter substantially equal to the inner diameter of the bellows forming portion. The heat exchange body 54 is formed by a metal material such as stainless steel or aluminum or a resin material such as polyethylene or polycarbonate. Metal materials such as stainless steel or aluminum are preferred from the viewpoint of strength and heat exchange efficiency. In particular, the bellows-type heat exchange body 54 is preferably formed by a metallic bellows tube in a corrugated form with multiple repeated convexes and concaves substantially orthogonal to the axial direction (central axis) of the heat exchange body 54.

Materials for the heat exchange housing 5, the heat medium chamber forming member 55, and the separation wall 56 may be, for example, polyolefin such as polyethylene or polypropylene, ester resin (for example, polyester such as polyethylene terephthalate or polybutylene terephthalate), styrene resin (for example, polystyrene, MS resin, MBS resin, ABS resin, BS resin), resin materials such as polycarbonate, various kinds of ceramics materials, metal materials, or the like.

A flow of heat medium in the heat exchange portion 1B of the oxygenator 1 will be described below with reference to FIGS. 1 to 3.

The heat medium flowing from the heat medium inlet port 52 first enters into the inlet-side heat medium chamber 57, flows into an outer peripheral side of the heat medium chamber forming member 55 through the opening 59a, spreads substantially within the entire outer periphery of the heat medium chamber forming member 55, and then enters into the multiple concaves in the bellows of the heat exchange body 54 (inside of the hollow annular projections). Accordingly, the heat exchange body 54 is heated or cooled in contact with the heat medium. Then, heat exchange (heating or cooling) is conducted between the heat exchange body 54 and the blood flowing on the outer peripheral side of the heat exchange body 54.

The heat medium used for heating or cooling of the heat exchange body 54 enters into the outlet-side heat medium chamber 58 through the opening 59b and is then discharged from the heat medium outlet port 53.

Unlike in the illustrated embodiment, the heat exchange portion 1B in accordance with a further example of the disclosure may be provided downstream of the oxygenating portion 1A. Further, the heat exchange portion 1B may not be provided at all in accordance with a still further example of the disclosure here.

A flow of blood in the oxygenator 1 of the embodiment will now be described. In the oxygenator 1, the blood flowing from the blood inlet port 51 flows into the blood chamber 50, that is, between the inner peripheral surface of the heat exchanger housing 5 and the heat exchange body 54, and contacts the outer surfaces of a plurality of hollow annular projections in the heat exchange body 54 to be subjected to heat exchange (heating or cooling). The blood having thus undergone heat exchange is collected on the downstream of the heat exchanger housing 50, and flows into the housing 2 of the oxygenating portion 1A through the blood inlet-side opening 24.

The blood having flowed through the blood inlet-side opening 24 flows through the blood passages 33 in the downstream direction. Meanwhile, gas (gaseous matter including oxygen) supplied from the gas inlet port 26 is distributed by the first chamber 221 into the gas passages 32 in the lumens of the hollow fiber membranes 31, flows through the gas passages 32, is accumulated in the second chamber 231, and is then discharged from the gas outlet port 27. The blood flowing through the blood passages 33 contacts the surfaces of the hollow fiber membranes 31 and is subjected to gas exchange (oxygenation and decarbonation) with the gas flowing through the gas passages 32.

When bubbles are mixed into the blood having undergone gas exchange, the bubbles are caught by the filter member 41 and thus do not flow out downstream of the filter member 41.

The blood having thus undergone gas exchange and bubble removal flows out from the blood outlet port 28.

In the oxygenator 1 of the exemplary embodiment described herein, it is preferred that blood-contacting surfaces (for example, the inner surface of the housing 2, the inner surface of the heat exchanger housing 5, the surface of the heat medium chamber forming member 55, and surfaces of the securing portions 7 and the partition walls 8 and 9 facing the blood passages 33) are made antithrombotic. The antithrombotic surfaces can be formed by an antithrombotic material being applied and fixed to the surfaces. The antithrombotic material may be heparin, urokinase, HEMA-St-HEMA copolymer, poly-HEMA, and the like.

In the oxygenator 1, the exemplary embodiment is not particularly limited on the flow rate of blood flowing from the blood inlet port 51 because the flow rate of blood may be different depending on a patient's physique and an operation procedure. In general, the flow rate of blood is preferably about 0.1 to 2.0 L/min for infants and young children, and preferably about 2.0 to 5.0 L/min for school children, and preferably about 3.0 to 7.0 L/min for adults.

In the oxygenator 1, the exemplary embodiment is also not particularly limited on the flow rate of gas supplied from the gas inlet port 26 because the flow rate of gas may be different depending on a patient's physique and an operation procedure. In general, the flow rate of gas is preferably about 0.05 to 4.0 L/min for infants and young children, and preferably about 1.0 to 10.0 L/min for school children, and preferably about 1.5 to 14.0 L/min for adults.

In addition, there is no particular limitation on the concentration of oxygen in the gas supplied from the gas inlet port 26 because the concentration of oxygen may be different depending on the metabolic amount of oxygen/carbon-dioxide gas of a patient under surgery. The concentration of oxygen can be 40 to 100%.

There is also no particular limitation on the maximum continuous operation time of the oxygenator 1 because the maximum continuous operation time may be different depending on a patient's condition and an operation procedure. In general, the maximum continuous operation time can be about 2 to 6 hours. In addition, the maximum continuous operation time of the oxygenator 1 may be as long as about 10 hours on rare occasions.

Figure 7:
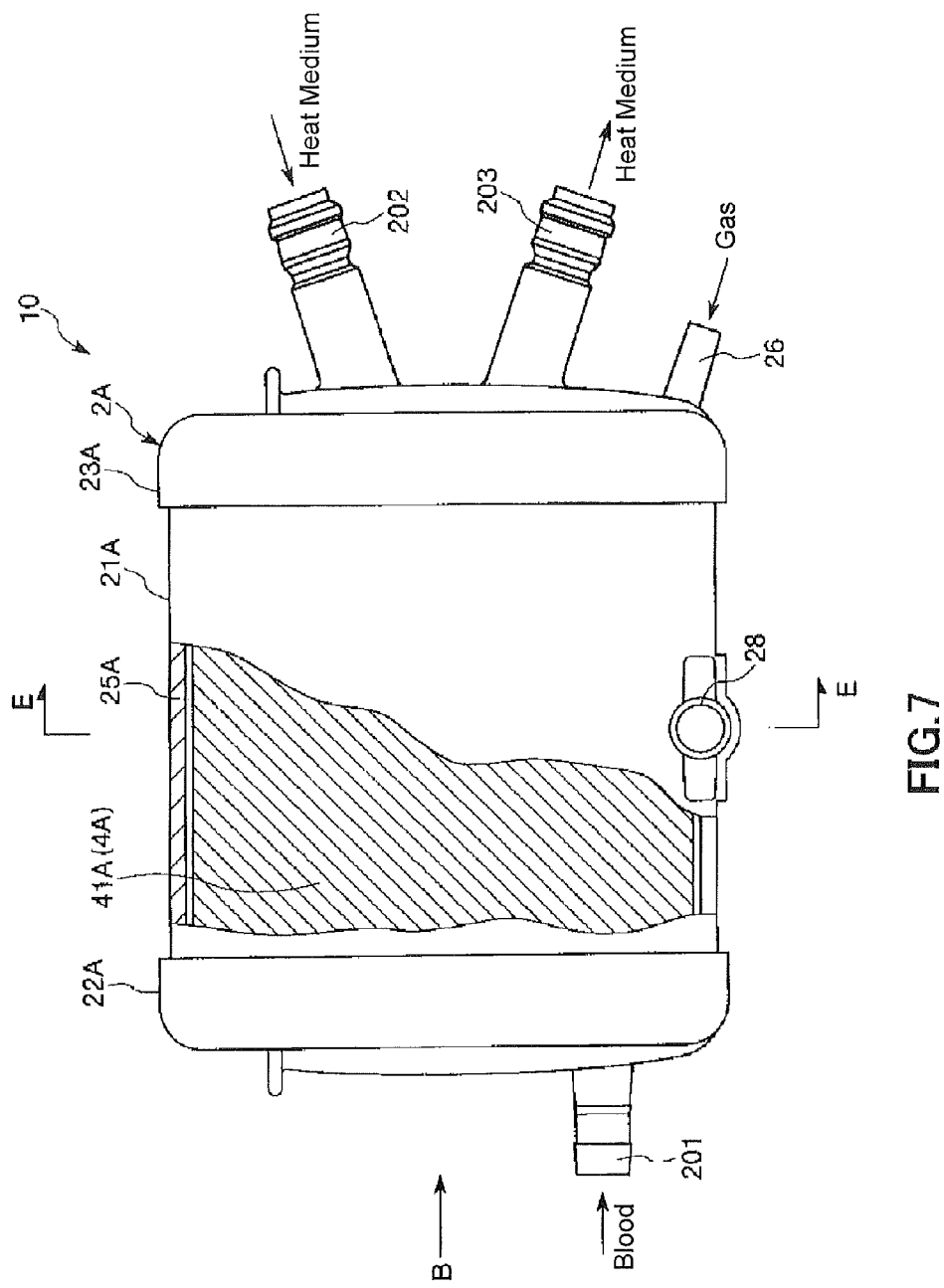
FIG. 7 is a plan view of a second exemplary embodiment of an oxygenator according to the disclosure.
Figure 8:
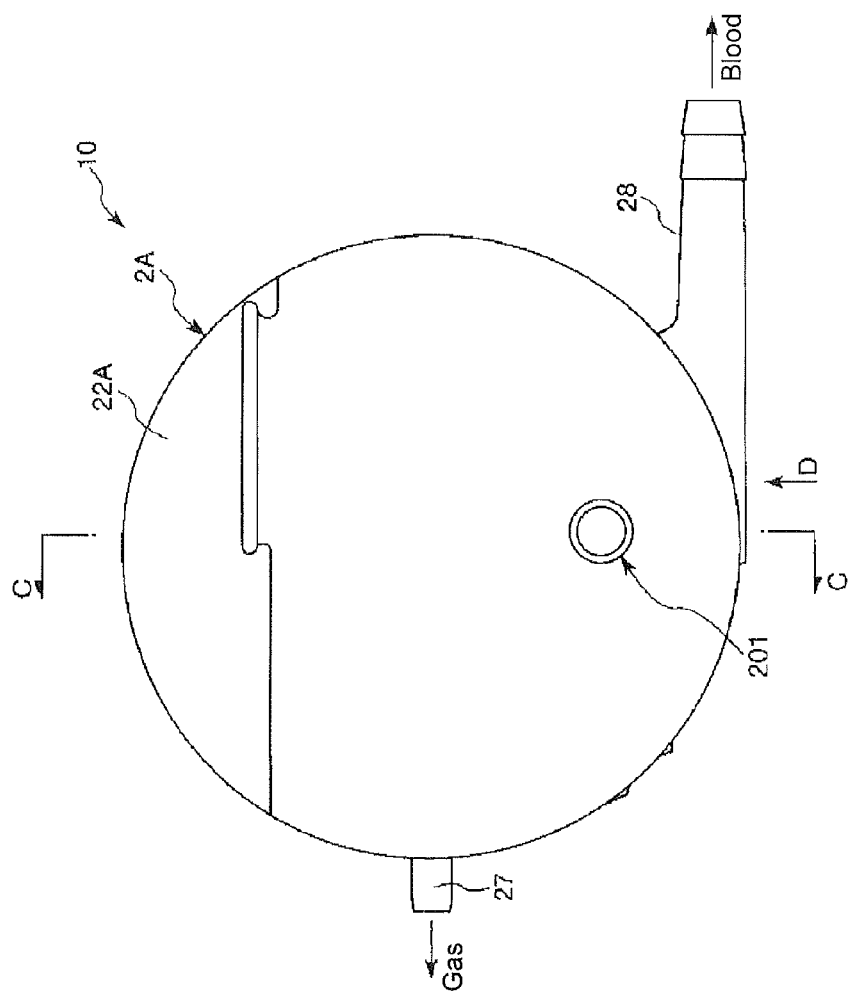
FIG. 8 is a view of the oxygenator illustrated in FIG. 7 as seen from arrow B.
Figure 9:
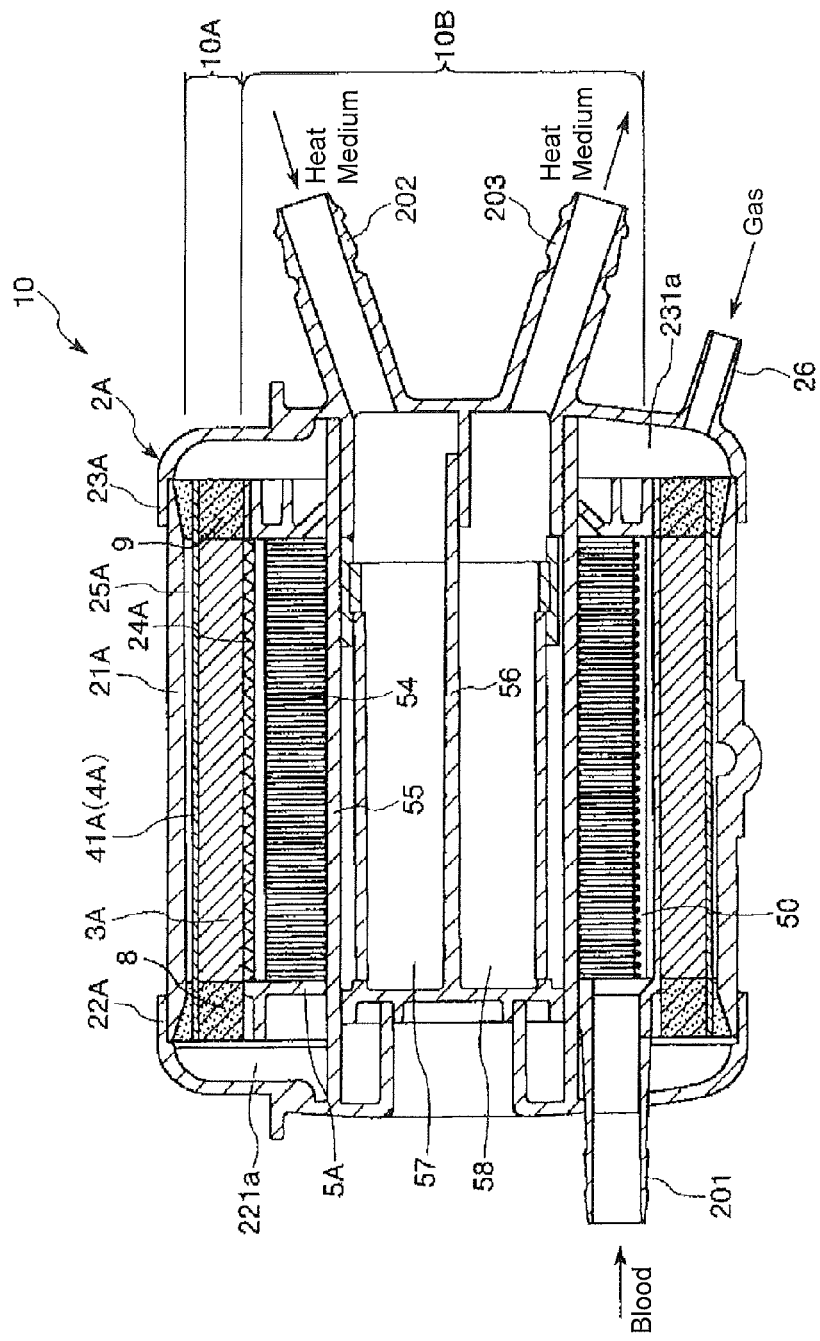
FIG. 9 is a cross section view of FIG. 8 taken along line C-C.
Figure 10:
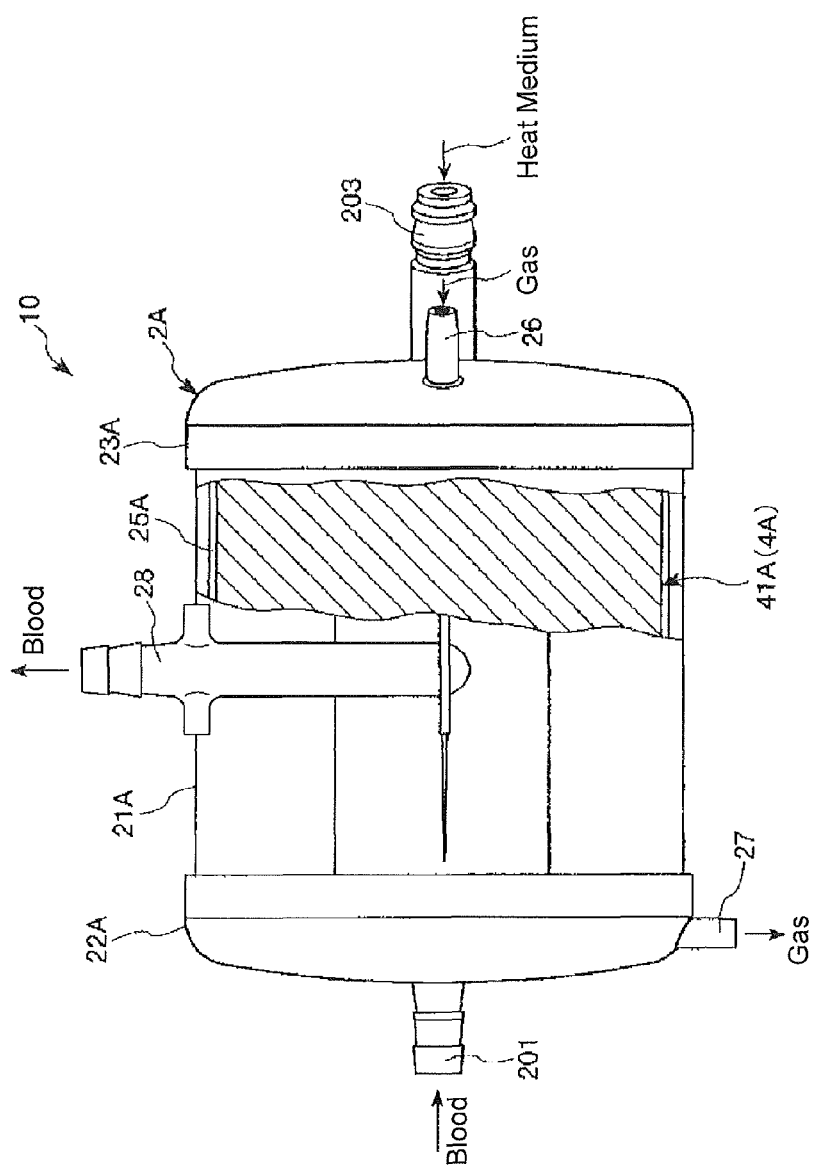
FIG. 10 is a view of FIG. 8 as seen from arrow D.

FIGS. 7-12 illustrate a second exemplary embodiment of an oxygenator according to the disclosure here. In FIGS. 7, 9, and 10, the left side is referred to as "left" or "left side," the right side is referred to as "right" or "right side." In FIGS. 7 to 12, the inside of the oxygenator is referred to as "blood inlet side" or "upstream," and the outside of the oxygenator is referred to as "blood outlet side" or "downstream."

The second exemplary embodiment of an oxygenator of the disclosure will be described below with reference to the foregoing diagrams. In the following, differences from the foregoing embodiment will be mainly described, and matters similar to those in the foregoing embodiment will be omitted.

The second exemplary embodiment is the same as the first exemplary embodiment except for the overall shape of an oxygenator.

The entire shape (outer shape) of an oxygenator 10 in the exemplary embodiment illustrated in FIGS. 7 to 12 is substantially columnar. The oxygenator 10 is a heat exchanger-equipped oxygenator including a heat exchange portion (heat exchanger) 10B provided inside thereof and configured in substantially the same manner as the heat exchanger portion 1B in the first embodiment, and an oxygenating portion 10A provided on an outer peripheral side of the heat exchange portion 10B and configured to conduct gas exchange with blood.

The oxygenator 1 has a housing 2A in which the oxygenating portion 10A and the heat exchange portion 10B are stored. The heat exchange portion 10B is further stored in a heat exchanger housing 5A in the housing 2A. The heat exchange portion 10B has opposite ends fixed to the housing 2A by the heat exchanger housing 5A.

The housing 2A is formed by a circular cylindrical housing body (hereinafter, referred to as "circular cylindrical housing body"), a dish-shaped first header (upper lid) 22A that closes a left end opening of the circular cylindrical housing body 21A, and a dish-shaped second header (lower lid) 23A that closes a right end opening of the circular cylindrical housing body 21A.

The circular cylindrical housing body 21A, the first header 22A, and the second header 23A are each formed by polyolefin such as polyethylene or polypropylene, ester resin (for example, polyester such as polyethylene terephthalate or polybutylene terephthalate), styrene resin (for example, polystyrene, MS resin, MBS resin, ABS resin, BS resin), resin materials such as polycarbonate, various kinds of ceramic materials, metal materials, or the like. The first header 22A and the second header 23A are secured to the circular cylindrical housing body 21A by adhesion means such as fusing, adhesion using an adhesive, or the like.

A tubular blood outlet port 28 is formed at an outer peripheral portion of the circular cylindrical housing body 21A. The blood outlet port 28 protrudes in a direction substantially tangent to the outer peripheral surface of the circular cylindrical housing body 21A (see FIG. 11).

A tubular blood inlet portion 201 and a gas outlet port 27 protrude from the first header 22A. The blood inlet portion 201 is formed on an end surface of the first header 22A such that a central axis thereof is located eccentrically with respect to the center of the first header 22A. The gas outlet port 27 is formed at an outer peripheral portion of the first header 22A such that a central axis thereof crosses the center of the first header 22A (see FIG. 8).

A tubular gas inlet port 26, a heat medium inlet port 202, and a heat medium outlet port 203 protrude from the second header 23A. The gas inlet portion 26 is formed at an edge portion of an end surface of the second header 23A. The heat medium inlet port 202 and the heat medium outlet port 203 are each formed at substantially the center portion of the end surface of the second header 23A. Center lines of the heat medium inlet port 202 and the heat medium outlet port 203 are slightly inclined with respect to the center line of the second header 23A.

In the disclosure here, the entire shape of the housing 2A is not necessarily a complete column, but the housing 2A may be partially cut away or provided with a different-shaped portion.

Figure 11:
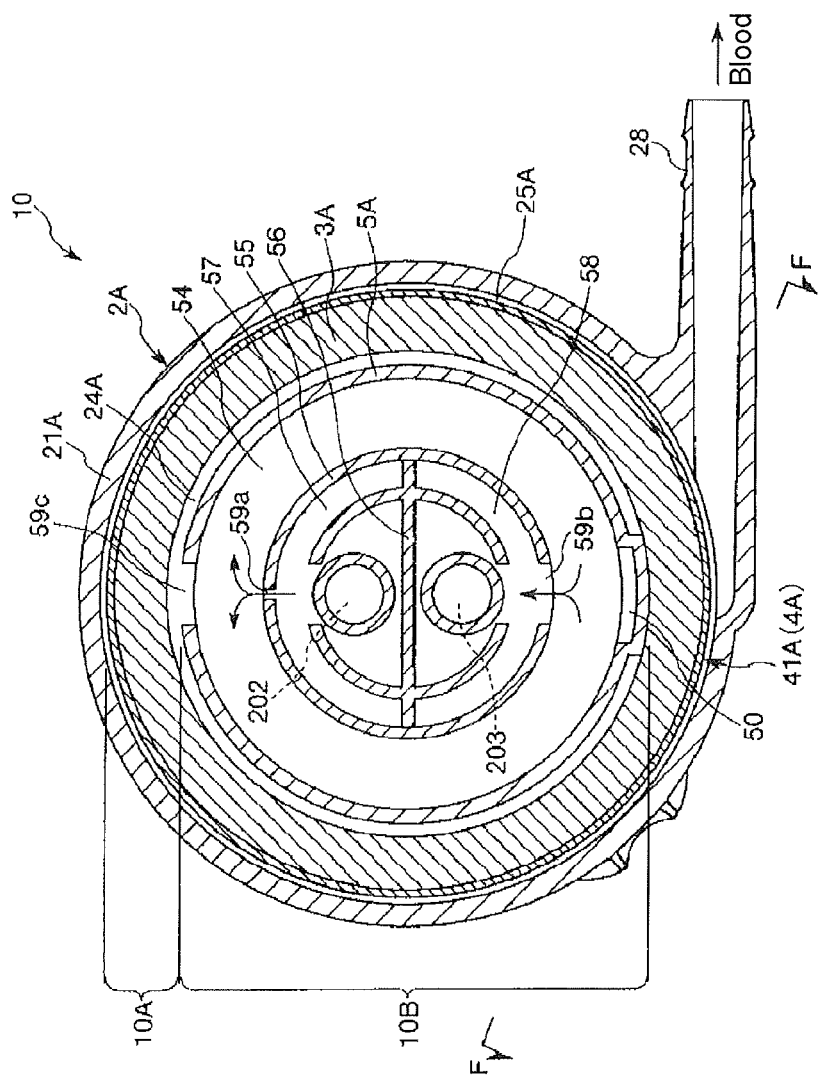
FIG. 11 is a cross section view of FIG. 7 taken along line E-E.

As illustrated in FIGS. 9 and 11, the housing 2A stores an oxygenating portion 10A shaped in a circular cylinder following an inner peripheral surface thereof. The oxygenating portion 10A is formed by a circular cylindrical hollow fiber membrane layer 3A, and a filter member 41A serving as bubble removal means 4A provided on an outer peripheral side (blood outlet portion side) of the hollow fiber membrane layer 3A. The hollow fiber membrane layer 3A and the filter member 41A are arranged from the blood inlet side in order of the hollow fiber membrane layer 3A and the filter member 41A.

Figure 12:
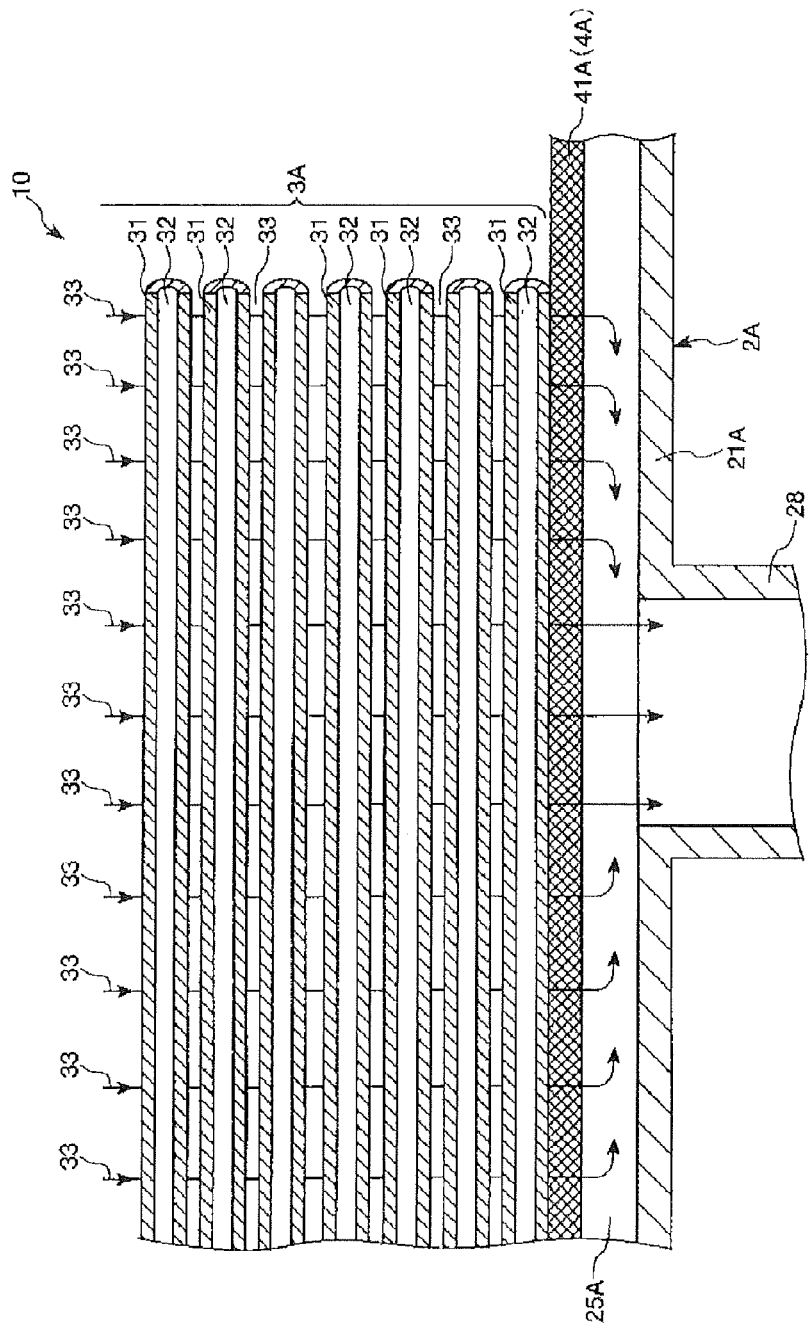
FIG. 12 is a cross section view of FIG. 11 taken along line F-F.

As illustrated FIG. 12, the hollow fiber membrane layer 3A includes multiple integrated hollow fiber membranes 31 having a gas exchange function. Most of the hollow fiber membranes 31 constituting the hollow fiber membrane layer 3A are disposed substantially parallel to the central axis of the housing 2A.

The arrangement pattern, arrangement direction, and the like of the hollow fiber membranes 31 in the hollow fiber membrane layer 3A are not limited to the aforementioned embodiments. For example, the hollow fiber membranes 31 may be arranged perpendicular to the central axis of the housing 2A, the hollow fiber membranes 31 may have portions at which the hollow fiber membranes 31 obliquely intersect one another (crossing portions), all or some of the hollow fiber membranes 31 may be curved, or all or some of the hollow fiber membranes 31 may be arranged in a corrugated, helical, spiral, or annular form.

As illustrated in FIG. 9, opposite end portions (left end portion (one end portion) and right end portion (the other end portion)) of the hollow fiber membranes 31 are fixed to the inner surface of the circular cylindrical housing body 21A by the partition walls 8 and 9. Accordingly, the relative position of both end portions of each hollow fiber membranes 31 is fixed.

The hollow fiber membrane layer 3A is filled between the circular cylindrical housing body 21A and the heat exchange portion 10B substantially without any empty space, and thus the hollow fiber membrane layer 3A is entirely shaped in substantially a circular cylinder. This provides high efficiency of filling the hollow fiber membranes 31 into the similarly shaped circular cylindrical housing body 21A (with less dead space), which contributes to a smaller size and higher performance of the oxygenating portion 10A.

The average separation distance $\epsilon$ [μm] between the adjacent hollow fiber membranes 31 at the portions of the hollow fiber membrane layer 3A fixed by the partition walls 8 and 9, the outer diameter OD [μm] of the hollow fiber membranes 31, the inter diameter ID [μm] of the hollow fiber membranes 31, and the effective length L [mm] of the hollow fiber membranes 31, are the same as those in the first exemplary embodiment as described above. Accordingly, it is possible to decrease the amount of blood filled in the oxygenating portion 10A and thus reduce the amount of blood filled in the oxygenator 10, without lowering gas exchange performance or increasing a pressure loss during flowing of the blood.

Although it is not particularly limited, the thickness of the hollow fiber membrane layer 3A (horizontal length in FIG. 11) is preferably about 2 to 100 mm, more preferably about 3 to 30 mm.

The hollow fiber membranes 31 are exposed between the partition walls 8 and 9 in the housing 2A to form blood passages 33 outside the hollow fiber membranes 31, that is, in the gaps between the hollow fiber membranes 31 to allow blood to flow from the upper to lower sides in FIG. 12.

Upstream of the blood passages 33 (on an upstream-side surface of the hollow fiber membrane layer 3A), that is, between the oxygenating portion 10A and the heat exchange portion 10B, a circular cylindrical blood inlet-side opening (blood inlet-side space) 24A is formed as a blood inlet portion for blood flowing from the blood inlet portion 201 (see FIGS. 9 and 11).

The blood having flown into the blood inlet-side opening 24A flows in the circumferential and longitudinal directions of the blood inlet-side opening 24A. Thus, the blood spreads within the entire blood inlet-side opening 24A. Accordingly, it is possible to efficiently transfer blood from the heat exchange portion 10B to the oxygenating portion 10A.

Downstream of the blood passages 33 (on the downstream-side surface of the hollow fiber membrane layer 3A), a circular cylindrical gap is formed between an outer peripheral surface of the filter member 41A described later and the inner peripheral surface of the square cylindrical housing body 21A. The gap constitutes a blood outlet-side opening (blood outlet-side space) 25A. The blood outlet-side opening 25A and the blood outlet port 28 communicating with the blood outlet-side opening 25A constitute a blood outlet portion. The blood outlet portion with the blood outlet-side opening 25A provides a space for the blood having flowed through the filter member 41A to flow toward the blood outlet port 28, thereby allowing smooth discharge of blood.

The hollow fiber membrane layer 3A, the filter member 41A, and the blood passages 33 are disposed between the blood inlet-side opening 24A and the blood outlet-side opening 25A.

As described above, the bubble removal means 4A with the function of catching bubbles in blood and removing the same from the blood, is provided downstream (blood outlet portion side) of the hollow fiber membrane layer 3A. The bubble removal means 4A has the filter member 41A.

The filter member 41A has the function of catching bubbles existing in blood flowing through the blood passages 33.

The filter member 41A is formed by a substantially rectangular, flat sheet-like member (hereinafter, also referred to simply as "sheet"). The filter member 41A is formed by winding a substantially rectangular sheet-like member (hereinafter, referred also to as simply "sheet") in a columnar shape. The first filter member 41A has opposite end portions adhered and fixed by the partition walls 8 and 9 to the housing 2A (see FIG. 9).

The filter member 41A has an inner peripheral surface thereof that is in contact with a surface downstream (blood outlet portion side) of the hollow fiber membrane layer 3A so as to substantially cover the entire surface. Providing the filter member 41A in this manner makes it possible to increase the effective area of the filter member 41A and allow the filter member 41A to exert a sufficient capability for catching bubbles. In addition, when the effective area of the filter member 41A is larger, even if the filter member 41A is partly clogged (with adhesion of clots of blood, for example), it is possible to prevent (suppress) interference with the entire flow of blood.

In the illustrated exemplary embodiment, the filter member 41A has a substantially constant outer diameter. However, the outer diameter of the filter member 41A is not limited thereto, and the filter member 41A may have an outer diameter partly increased or decreased.

The oxygenator 10 having the thus arranged filter member 41A is used in a configuration illustrated in FIGS. 7 to 9 and 11. In this case, the blood outlet port 28 is located at a vertically lower position at use of the oxygenator 10. Specifically, the lumen of the blood outlet port 28 communicates with the lower portion of the blood outlet-side opening 25A. Accordingly, the blood having flowed through the filter member 41A and entered into the blood outlet-side opening 25A flows toward the blood outlet port 28 in the blood outlet-side opening 25A, and then flows out from the blood outlet port 28 to the outside of the housing 2.

Even when bubbles exist in the blood flowing through the blood passages 33, the filter member 41A can catch the bubbles. In addition, the bubbles caught by the filter member 41A are pressed and entered by the blood into the hollow fiber membranes 31 near the filter member 41A, and as a result, the bubbles are removed from the blood passages 33.

As illustrated in FIG. 9, a first chamber 221a is defined by the first header 22A, the partition wall 8, and the heat exchanger housing 5A and the heat medium chamber forming member 55 of the heat exchange portion 10B. The first chamber 221a is a gas outlet chamber from which gas flows out. The hollow fiber membranes 31 have left end openings opened to and communicating with the first chamber 221a.

A second chamber 231a is defined by the second header 23A, the partition wall 9, and the heat exchanger housing 5A and the heat medium chamber forming member 55 of the heat exchange portion 10B. The second chamber 231a is a gas inlet chamber into which gas flows. The hollow fiber membranes 31 have right end openings opened to and communicating with the second chamber 231a.

Lumens of the hollow fiber membranes 31 form gas passages 32 through which gas flows. The gas inlet port 26 and the second chamber 231a constitute a gas inlet portion located on the upstream side of the gas passages 32. The gas outlet port 27 and the first chamber 221a constitute a gas outlet portion located on the downstream side of the gas passages 32.

As described above, the heat exchange portion 10B is provided inside of the oxygenating portion 10A. The heat exchange portion 10B is configured in substantially the same manner as the heat exchange portion 1B, and thus a description thereof will be omitted.

Placing the heat exchange portion 10B inside of the oxygenating portion 10A provides a number of advantages. Specifically, the oxygenating portion 10A and the heat exchange portion 10B can be efficiently stored in one housing 2A with less dead space, thereby realizing efficient gas exchange in the small-sized oxygenator 10. Further, the oxygenating portion 10A and the heat exchange portion 10B are closer to each other than those in the first exemplary embodiment, which allows the blood having undergone heat exchange at the heat exchange portion 10B to flow quickly into the oxygenating portion 10A. This makes it possible to minimize the amount of blood filled into the blood inlet-side opening 24A (blood passages 33) connecting the heat exchange portion 10B and the oxygenating portion 10A. In addition, the blood having undergone heat exchange at the heat exchange portion 10B can flow quickly into the oxygenating portion 10A without being subjected to heat release or heat absorption.

Next, a flow of blood in the oxygenator 10 of the second exemplary embodiment will be described.

In the oxygenator 10, the blood flowing from the blood inlet port 201 flows into the blood chamber 50, that is, between the inner peripheral surface of the heat exchanger housing 5A and the heat exchange body 54, and contacts the outer surfaces of a plurality of hollow annular projections in the heat exchange body 54 to be subjected to heat exchange (heating or cooling). The blood thus having undergone heat exchange sequentially flows through the opening 59c formed at the upper portion of the heat exchanger housing 5A and the blood inlet-side opening 24A in sequence, and flows into the housing 2A of the oxygenating portion 10A.

The blood having flowed through the blood inlet-side opening 24A flows through the blood passages 33 in the downstream direction. Meanwhile, gas (gaseous matter including oxygen) supplied from the gas inlet port 26 is distributed by the second chamber 231a into the gas passages 32 in the lumens of the hollow fiber membranes 31, flows through the gas passages 32, is accumulated in the first chamber 221a, and then is discharged from the gas outlet port 27. The blood flowing through the blood passages 33 contacts the surfaces of the hollow fiber membranes 31 and is subjected to gas exchange (oxygenation and decarbonation) with the gas flowing through the gas passages 32.

When bubbles are mixed into the blood having undergone gas exchange, the bubbles are caught by the filter member 41A and thus do not flow out downstream of the filter member 41A.

The blood having thus undergone gas exchange and bubble removal flows out from the blood outlet port 28.

In the oxygenator 10, providing the hollow fiber membrane layer 3A makes it possible to set the amount of blood filled in the oxygenating portion 10A per unit membrane area of the oxygenator 10 at, for example, about 25 to 50 mL/m$^2$, in particular, about 30 to 45 mL/m$^2$.

Therefore, the amount of blood filled in the oxygenator 10 may be, for example, about 30 to 90 mL/m$^2$, in particular, 35 to 85 mL/m$^2$, although depending on the amount of blood filled in the heat exchange portion 10B and the like.

As in the foregoing, the illustrated exemplary embodiments of the oxygenator of the disclosure are described. However, the disclosure here is not limited to the foregoing, and the components thereof can be replaced with arbitrary components with the same functions. In addition, any other arbitrary component can be added to the present invention.

For example, the structures and shapes of the housing and the heat exchanger, and the formation positions and protrusion directions of the gas inlet port, gas outlet port, blood outlet port, blood inlet port, heat medium inlet port, and heat medium outlet portion, and the like, may be different from those of the illustrated configurations. In addition, the orientation of the oxygenator during use (vertical position relationships between the components) is not limited to the illustrated state.

The oxygenator in the disclosure may be a combination of two or more arbitrary configurations (features) in the foregoing embodiments.

In addition, the oxygenator of the second exemplary embodiment allows blood to flow through from inside to outside. However, the oxygenator is not limited thereto and may alternatively be configured to allow blood to flow through from outside to inside. In this case, the filter member is arranged in contact with the inner peripheral portion of the circular cylindrical hollow fiber membrane layer.

Specific examples of the exemplary embodiments will be described below.

EXAMPLE 1

The oxygenator illustrated in FIGS. 7 to 12 was manufactured. Polypropylene was used as a constituent material for the hollow fiber membranes of the hollow fiber membrane layer. The dimensions of the hollow fiber membranes are as follows:
Average separation distance $\epsilon$: 60 μm
Outer diameter OD: 200 μm
OD/$\epsilon$: 3.3
Inner diameter ID: 140 μm
Effective length L: 170 mm

EXAMPLE 2

An oxygenator was obtained with a hollow fiber membrane layer formed in the same manner as that of Example 1, except for changing the dimensions of the hollow fiber membranes as follows:
Average separation distance $\epsilon$: 46 μm
Outer diameter OD: 200 μm
OD/$\epsilon$: 4.3
Inner diameter ID: 140 μm
Effective length L: 170 mm

EXAMPLE 3

An oxygenator was obtained with a hollow fiber membrane layer formed in the same manner as that of Example 1, except for changing the dimensions of the hollow fiber membranes as follows:

Average separation distance ε: 46 μm
Outer diameter OD: 170 μm
OD/ε: 3.7
Inner diameter ID: 110 μm
Effective length L: 116 mm

EXAMPLE 4

An oxygenator was obtained with a hollow fiber membrane layer formed in the same manner as that of Example 1, except for changing the dimensions of the hollow fiber membranes as follows:
Average separation distance ε: 46 μm
Outer diameter OD: 150 μm
OD/ε: 3.3
Inner diameter ID: 90 μm
Effective length L: 116 mm

EXAMPLE 5

An oxygenator was obtained with a hollow fiber membrane layer formed in the same manner as that of Example 1, except for changing the dimensions of the hollow fiber membranes as follows:
Average separation distance ε: 30 μm
Outer diameter OD: 130 μm
OD/ε: 4.3
Inner diameter ID: 90 μm
Effective length L: 116 mm

COMPARATIVE EXAMPLE 1

An oxygenator was obtained with a hollow fiber membrane layer formed in the same manner as that of Example 1, except for changing the dimensions of the hollow fiber membranes as follows:
Average separation distance ε: 46 μm
Outer diameter OD: 295 μm
OD/ε: 6.4
Inner diameter ID: 195 μm
Effective length L: 194 mm

COMPARATIVE EXAMPLE 2

An oxygenator was obtained with a hollow fiber membrane layer formed in the same manner as that of Example 1, except for changing the dimensions of the hollow fiber membranes as follows:
Average separation distance ε: 30 μm
Outer diameter OD: 200 μm
OD/ε: 6.7
Inner diameter ID: 140 μm
Effective length L: 170 mm

COMPARATIVE EXAMPLE 3

An oxygenator was obtained with a hollow fiber membrane layer formed in the same manner as that of Example 1, except for changing the dimensions of the hollow fiber membranes as follows:
Average separation distance ε: 60 μm
Outer diameter OD: 295 μm
OD/ε: 4.9
Inner diameter ID: 195 μm
Effective length L: 194 mm EXAMPLES 1 to 5 and Comparative Examples 1 to 3 were each subjected to the following measurements. Results of the measurements are as shown below in Table 1.

<Gas Exchange Performance>

Cow blood and oxygen adjusted under the following conditions were put into the oxygenator, and then the hemoglobin content of the blood, oxygen saturation and oxygen partial pressure in the blood before flowing into the oxygenator, and oxygen saturation and oxygen partial pressure in the blood flowing out from the oxygenator were measured. The amount of oxygen movement was obtained as gas exchange performance by Equation (1) as follows:

$$\text{Amount of oxygen movement} = 1.34 \times Hb \times Qb \times 1000 \times (SaO_2 - SvO_2)/10000 + (PaO_2 - PvO_2) \times Qb \times 1000 \times 0.0031/100 \quad (1)$$

In Equation (1),
Hb: Hemoglobin concentration
Qb: Flow rate of blood
$SaO_2$: Oxygen saturation in the blood flowing out from the oxygenator
$SvO_2$: Oxygen saturation in the blood flowing into the oxygenator
$PaO_2$: Oxygen partial pressure in the blood flowing out form the oxygenator
$PvO_2$: Oxygen partial pressure in the blood flowing into the oxygenator The $SaO_2$, $SvO_2$, $PaO_2$, $PvO_2$, and Hb are each measurement values. In general, although Hb is 12±1 [g/dL], $SvO_2$ is 65±5 [%], and $PvO_2$ is 45±5 [mmHg], the measurement values were used for these parameters.

The content of oxygen was set at 100 [%], the flow rate of oxygen at 7 [L/min], the temperature of the blood at 37±1 [°C.], and the flow rate of blood at 7 [L/min]. The V/Q ratio (flow rate of oxygen/flow rate of blood) was 1.

<Pressure Loss>

Cow blood adjusted under the following conditions was flowed into the oxygenator, a pressure of the blood before flowing into the oxygenator and a pressure of the blood after flowing out from the oxygenator were measured, and then a difference in pressure between the two, that is, a pressure loss was obtained. The temperature of the blood was set at 37±1 [°C.], and the flow rate of blood at 7 [L/min]. In addition, hematocrit value was 35±1 [%].

As an evaluation criterion for pressure loss, a pressure loss of 250 mmHg or less is regarded as good and a pressure loss exceeding 250 mmHg as not good, for clinical use.

<Filling Amount>

Water was filled into the oxygenator, and the weight of the oxygenator before the filling of the water and the weight of the oxygenator after the filling of the water were measured, and the filling amount was obtained from a difference in weight between the two.

The filling amount in the entire oxygenator, the filling amount in the oxygenating portion, and the filling amount per unit membrane area in the oxygenating portion, were measured.

The filling amount in the entire oxygenator of Comparative Example 1 as a conventional product was 250 mL, and thus as an evaluation criteria for filling amount in the entire oxygenator, a filling amount of less than 250 mL is regarded as good, and a filling amount of 250 mL or more as not good.

In addition, when both the pressure loss and the filling amount in the entire oxygenator are good, the oxygenator is regarded as "good," and when at least one of the two is not good, the oxygenator is regarded as "not good."

TABLE 1

|  | Average separation distance ϵ [μm] | Outer Diameter OD [μm] | OD/ϵ | Inner Diameter ID [μm] | Effective Length L [mm] | Amount of movement of oxygen [ml/min.] | Pressure Loss [mmHg] | Filling amount in entire oxygenator [ml] | Filling amount in oxygenating portion [ml] | Membrane area [m²] | Filling amount per unit membrane area in oxygenation portion [ml/m²] |
|---|---|---|---|---|---|---|---|---|---|---|---|
| Example 1 | 60 | 200 | 3.3 | 140 | 170 | 455 | 57 | 209 | 97 | 2.2 | 44.1 |
| Example 2 | 46 | 200 | 4.3 | 140 | 170 | 455 | 110 | 194 | 82 | 2.0 | 41.0 |
| Example 3 | 46 | 170 | 3.7 | 110 | 116 | 455 | 110 | 186 | 74 | 1.9 | 38.9 |
| Example 4 | 46 | 150 | 3.3 | 90 | 116 | 455 | 110 | 176 | 64 | 1.9 | 33.7 |
| Example 5 | 30 | 130 | 4.3 | 90 | 116 | 455 | 170 | 173 | 61 | 1.9 | 32.1 |
| Comparative Example 1 | 46 | 295 | 6.4 | 195 | 194 | 455 | 110 | 250 | 138 | 2.5 | 55.2 |
| Comparative Example 2 | 30 | 200 | 6.7 | 140 | 170 | 455 | 285 | 193 | 81 | 2.0 | 40.5 |
| Comparative Example 3 | 60 | 295 | 4.9 | 195 | 194 | 455 | 103 | 336 | 224 | 2.8 | 80.0 |

As shown in Table 1, Comparative Example 1 produced satisfying results for the amount of movement of oxygen and pressure loss, but caused large filling amounts.

Comparative Example 2 produced satisfying results for the amount of movement of oxygen and the filling amounts, but caused a large pressure loss.

Comparative Example 3 produced satisfying results for the amount of movement of oxygen and the pressure loss, but caused large filling amounts.

In contrast, Examples 1 to 5 yielded satisfying results for the amount of movement of oxygen, the pressure loss, and the filling amounts.

In Example 3, for example, while the amount of movement of oxygen and the pressure loss were equal to those in Comparative Example 1, the filling amount in the entire oxygenator was reduced to 74% of that in Comparative Example 1, the filling amount in the oxygenating portion was reduced to 54% of that in Comparative Example 1, and the filling amount per unit membrane area in the oxygenating portion was reduced to 70% of that in Comparative Example 1.

According to the disclosure, it is possible to provide an oxygenator with excellent gas exchange performance that produces a relatively small pressure loss during flowing of blood and needs a small filling amount of blood.

The detailed description above describes an oxygenator disclosed by way of example. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An oxygenator, comprising:
   a housing;
   a hollow fiber membrane layer that is stored in the housing and possesses multiple integrated hollow fiber membranes with a gas exchange function;
   a gas inlet portion and a gas outlet portion that are provided on the upstream and downstream of gas passages in lumens of the hollow fiber membranes, respectively;
   a blood inlet portion and a blood outlet portion that are provided on the upstream and downstream of blood passages outsides of the hollow fiber membranes, respectively;
   wherein the hollow fiber membranes in the hollow fiber membrane layer each possess first and second end portions, and are fixed to each other at the first end portions and the second end portions; and
   wherein condition (a) 30 ≤ϵ≤ 60 and condition (b) OD≤4.5×ϵ are met where ϵ [μm] is an average separation distance between the adjacent hollow fiber membranes at a fixed portion of the hollow fiber membrane layer and OD [μm] is the outer diameter of the hollow fiber membranes, and condition (c) L≤1.3×ID is met where ID [μm] is the inner diameter of the hollow fiber membranes and L [mm] is the length of the hollow fiber membranes contributing to gas exchange, such that, when conditions 120 ≤OD ≤220, (a), (b) and (c) are met and blood is introduced into the housing, the ratio of blood in the housing to membrane surface area in contact with the blood is in the range of 25 to 50 mL/m² without lowering a performance of the gas exchange function of the hollow fiber membranes.

2. The oxygenator according to claim 1, wherein, condition 0.55 ×OD ≤ID ≤0.8 ×OD is met where ID [μm] is the inner diameter of the hollow fiber membranes.

3. The oxygenator according to claim 1, wherein the hollow fiber membranes are formed by porous polypropylene or polymethylpentene.

4. The oxygenator according to claim 1, wherein the entire shape of the hollow fiber membrane layer is substantially cuboidal.

5. The oxygenator according to claim 1, wherein the entire shape of the hollow fiber membrane layer is substantially circular cylindrical.

6. The oxygenator according to claim 1, further comprising a heat exchanger including a heat exchanger housing, said heat exchanger housing being joined with said housing.

7. An oxygenator, comprising:
   an oxygenator portion including:
      a housing;
      a hollow fiber membrane layer that is stored in the housing and possesses multiple integrated hollow fiber membranes with a gas exchange function;
      a gas inlet portion and a gas outlet portion that are provided on the upstream and downstream of gas passages in lumens of the hollow fiber membranes, respectively;
      a blood inlet portion and a blood outlet portion that are provided on the upstream and downstream of blood passages outsides of the hollow fiber membranes, respectively;
      wherein the hollow fiber membranes in the hollow fiber membrane layer each possess first and second end portions, and are fixed to each other at the first end portions and the second end portions; and wherein conditions $30 \leq \epsilon \leq 60$ and $OD \leq 4.5 \times \epsilon$ are met where $\epsilon$[μm] is an average separation distance between the adjacent hollow fiber membranes at a fixed portion of the hollow fiber membrane layer and OD [μm] is the outer diameter of the hollow fiber membranes and condition $L \leq 1.3 \times ID$ is met where ID [μm] is the inner diameter of the hollow fiber membranes and L [mm] is the length of the hollow fiber membranes contributing to gas exchange, such that, when conditions $120 \leq OD \leq 220$, $30 \leq \epsilon \leq 60$, $OD \leq 4.5 \times \epsilon$, and $L \leq 1.3 \times ID$ are met and blood is introduced into the housing, the ratio of blood in the housing to membrane surface area in contact with the blood is in the range of 25 to 50mL/m² without lowering a performance of the gas exchange function of the hollow fiber membranes; and a heat exchanger portion including:
  a heat exchanger housing joined with said housing; and
  a heat exchange body arranged within said heat exchanger housing.

8. The oxygenator according to claim 7, wherein, the average separation distance between the adjacent hollow fiber membranes is met by the conditions $35 \leq \epsilon \leq 50$ and $120 \leq OD \leq 220$.

9. The oxygenator according to claim 7, wherein, condition $0.55 \times OD \leq ID \leq 0.8 \times OD$ is met where ID [μm] is the inner diameter of the hollow fiber membranes.

10. The oxygenator according to claim 9, wherein, the inner diameter of the hollow fiber membranes is met by the condition $60 \leq ID \leq 160$.

11. The oxygenator according to claim 7, wherein the hollow fiber membranes are formed by porous polypropylene or polymethylpentene.

12. The oxygenator according to claim 7, wherein the entire shape of the hollow fiber membrane layer is substantially cuboidal.

13. The oxygenator according to claim 7, wherein the entire shape of the hollow fiber membrane layer is substantially circular cylindrical.

14. The oxygenator according to claim 7, wherein said housing and said heat exchanger housing are integrated together.

* * * * *